United States Patent [19]
Andrews

[11] 3,930,311
[45] Jan. 6, 1976

[54] REINFORCED ORTHODONTIC BRACKET

[76] Inventor: Lawrence F. Andrews, 2025 Chatsworth Blvd., San Diego, Calif. 92107

[22] Filed: Dec. 20, 1973

[21] Appl. No.: 426,487

[52] U.S. Cl. ............................................. 32/14 A
[51] Int. Cl.² ......................................... A61C 7/00
[58] Field of Search ................................. 32/14 A

[56] References Cited
UNITED STATES PATENTS

| | | | |
|---|---|---|---|
| 3,250,003 | 5/1966 | Collito | 32/14 A |
| 3,469,314 | 9/1969 | Pearlman | 32/14 A |
| 3,504,438 | 4/1970 | Wittman et al. | 32/14 A |
| 3,765,091 | 10/1973 | Northcutt | 32/14 A |

*Primary Examiner*—Louis G. Mancene
*Assistant Examiner*—J. Q. Lever
*Attorney, Agent, or Firm*—Richard K. Macneill

[57] ABSTRACT

A reinforced orthodontic bracket constructed of a translucent plastic for direct application to a patient's tooth as by an adhesive where the translucent bracket itself has a metallic reinforcement imbedded therein for added structural strength for the prevention of a displacement of the bracket because of forces applied by an arch wire attached thereto.

1 Claim, 17 Drawing Figures

3,930,311

REINFORCED ORTHODONTIC BRACKET

BRIEF DESCRIPTION OF THE INVENTION

The present invention relates to a structurally reinforced orthodontic bracket.

According to the invention, an orthodontic bracket is provided which is non-metallic in structure such as a translucent plastic bracket directly applied to the tooth by an adhesive. One problem encountered with this type of bracket, while aesthetically pleasing, is the tendency of the plastic to distort excessively and, in some cases, actually fracture when forces are applied via an arch wire attached thereto. To obviate this, the current invention utilizes a stiffening core which is constructed of a more rigid material, such as metal, which is imbedded into the material of the bracket during the manufacture thereof, such as molding. The stiffening core surrounds the arch wire slots and can extend into the tie wing areas of the brackets.

An object of the present invention is the provision of a structurally reinforced orthodontic bracket.

Another object of the invention is the provision of an orthodontic bracket having a stiffening core imbedded therein.

A further object of the invention is the provision of a directly applied orthodontic bracket which is aesthetically pleasing and has structural integrity.

Other objects and many of the attendant advantages of the present invention will be readily appreciated as the same becomes better understood by reference to the following detailed description when considered in connection with the accompanying drawings in which like reference numerals designate like parts throughout the Figures thereof and wherein.

DETAILED DESCRIPTION OF THE DRAWING

Figure 1:
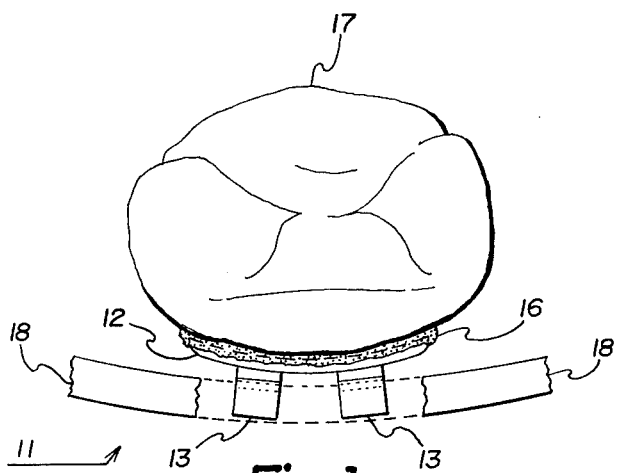
FIG. 1 is a plan view of a prior art orthodontic bracket directly attached to a tooth.
Figure 3:
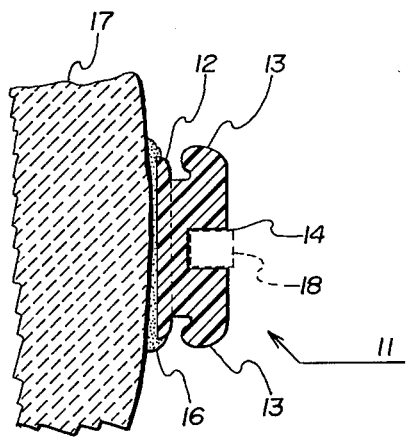
FIG. 3 is a sectional view taken along lines 3 — 3 of FIG. 2.
Figure 2:
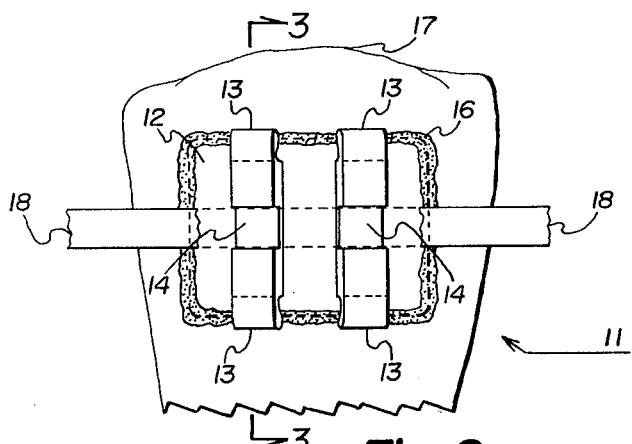
FIG. 2 is a front elevational view of the prior art bracket of FIG. 1.

Referring to FIGS. 1, 2 and 3, a non-metallic, e.g., plastic orthodontic bracket is shown generally at 11 having a base 12 and paired tie wings 13, together with an arch wire slot 14 therebetween. Base 12 is coupled via an adhesive 16 directly to a tooth 17. Arch wire 18 is shown inserted within arch wire slots 14.

Figure 6:
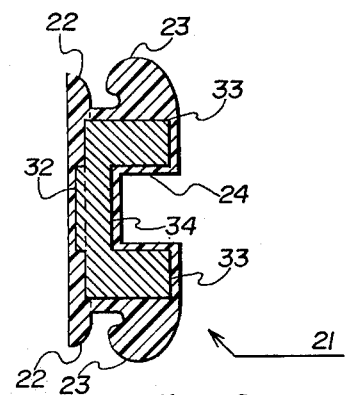
FIG. 6 is a sectional view taken along lines 6 — 6 of FIG. 4.
Figure 4:
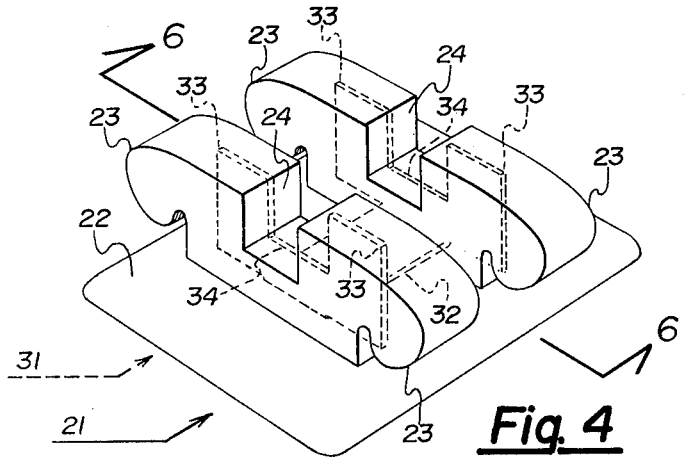
FIG. 4 is a perspective view of a reinforced bracket of the present invention.
Figure 5:
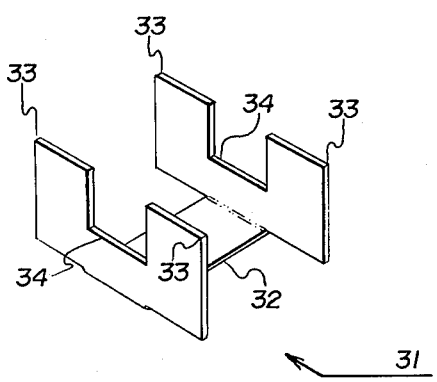
FIG. 5 is a perspective view of the reinforcing core of the embodiment of FIG. 4.

Referring to FIGS. 4, 5 and 6, directly applied bracket 21 has a base 22 which is adapted for being secured directly through an adhesive (not shown), to a tooth (not shown), as base 12 is shown in FIGS. 1, 2 and 3. A plurality of paired tie wings 23 are separated by arch wire slots 24. A stiffening core 31, which is preferably constructed of metal, is shown completely imbedded within bracket 21. Stiffening core 31 has core base 32 with riser sections 33 on each side of arch wire slot 24 and slot stiffener sections 34 below slots 24.

Figure 7:
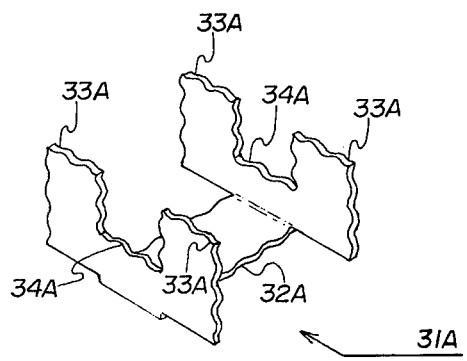
FIG. 7 is a perspective view of another embodiment of the reinforcing core of FIG. 5.

Referring to FIG. 7, a stiffener core is shown at 31A having a core base 32A with riser reinforcements 33A which would extend on each side of a wire slot in a bracket similar to that shown in FIGS. 4 and 6. Slot stiffeners 34A would extend below the arch wire slot in a bracket such as that shown in FIGS. 4 and 6. The difference between the core of FIG. 7 and that of FIG. 5 lies in the edge serrations which effect a more firm bonding within the plastic body of an orthodontic bracket in which it is imbedded.

Figure 8:
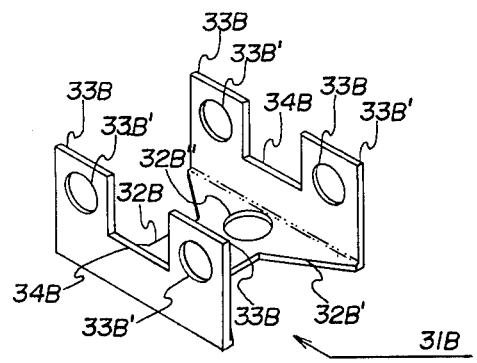
FIG. 8 is a perspective view of still another embodiment of the reinforcing core of FIG. 5.

Referring to FIG. 8, a core stiffener 31B is shown having a base 32B with an angled stiffening section 32B' together with a base aperture 32B''. Riser reinforcement sections 33B extend on each side of a wire slot of a bracket and have apertures 33B' therein. Arch wire slot stiffeners 34B are disposed beneath the arch wire slot in bracket 31B.

Figure 9:
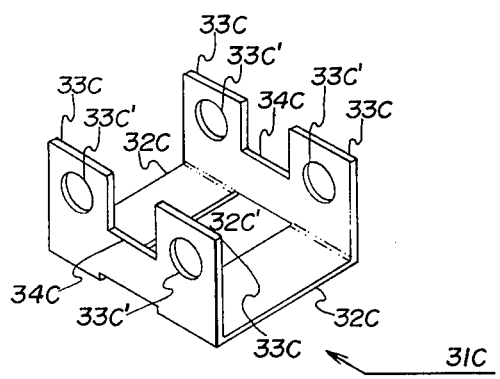
FIG. 9 is a perspective view of yet another embodiment of the reinforcing bracket of FIG. 5.

Referring to FIG. 9, a further modification of a stiffening core is shown at 31C having a split core base 32C which creates a core base slot 32C'. Riser reinforcements 33C have apertures 33C' therein. Slot stiffeners 34C have upper edges which are coplanar with the base of an arch wire slot such as 24 in FIGS. 4, 5 and 6.

Figure 10:
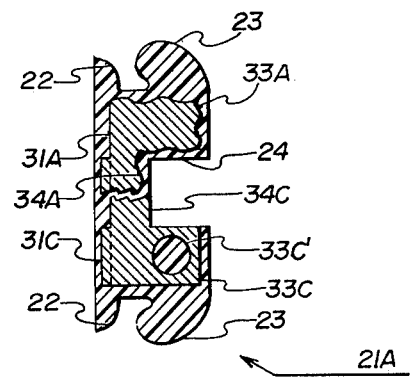
FIG. 10 is a sectional view illustrating the embodiments of FIGS. 7 and 9 in situ.

Referring to FIG. 10, a comparative cross section of a bracket such as 21 in FIGS. 4, 5 and 6 is shown at 21A with juxtaposed halves of the core embodiments 31A and 31C of FIGS. 7 and 9. Here the base is again shown at 22 with tie wings 23 and arch wire slot 24. Core stiffener section 31A is shown having riser 33A. Stiffening core section 31C is shown having riser 33C and aperture 33C'. It is pointed out that the slot stiffener 34C has one edge coplanar with the inner surface of arch wire slot 24 in bracket 21A.

Figure 11:
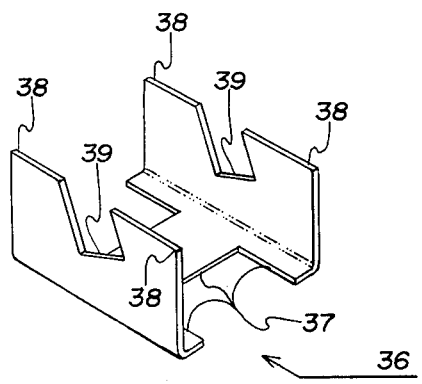
FIG. 11 illustrates in perspective a reinforcement core for utilization with a bracket having a torque angle built into the slot portion.

Referring to FIG. 11, a stiffening core 36 is shown having an angle stiffened core base 37 with risers 38 with a torque slot stiffener 39 oriented to be coplanar with the edges of a wire slot in a torquing bracket (not shown).

Figure 12:
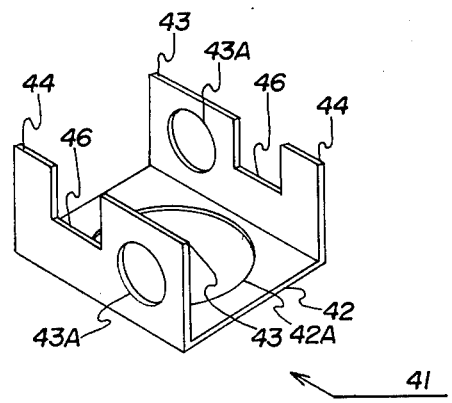
FIG. 12 is a perspective view of a reinforcement core for utilization with a bracket having a tip angle included therein.

Referring to FIG. 12, a stiffening core 41 is shown having a base 42 with an aperture 42A therein. Wide risers 43 have apertures 43A therein and are separated from narrow risers 44 by slot stiffener sections 46 which are offset for utilization in a tipping bracket (not shown).

Figures 13, 14:
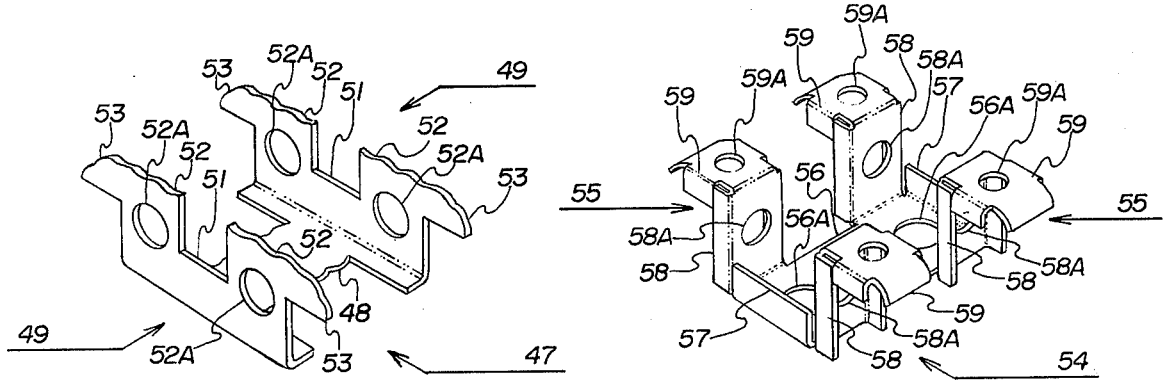
FIG. 13 is a perspective view of a reinforcement core having reinforcements in a tie wing portion.
FIG. 14 is a perspective view of another reinforcement core having reinforcement in the tie wing portion.

Referring to FIG. 13, a stiffening core 47 has a core base 48 terminating in each end by core riser assemblies 49. Core riser assemblies 49 each consist of a central slot stiffener 51 separating slot reinforcement risers 52 having apertures 52A. Tie wing reinforcement sections 53 extend from slot reinforcement risers 52.

Referring to FIG. 14, a stiffening core is shown at 54 having an elongated core base 56 with apertures 56A therein. Base 56 terminates on two opposite ends with slot reinforcing risers 57. Base 56 separates core risers 55 on opposite sides thereof. Core risers 55 terminate on their side portions with reinforcement tabs 58 and have apertures 58A therein. Risers 55 terminate at their top portions with tie wing tabs 59, each having an aperture 59A.

Figures 15, 16:
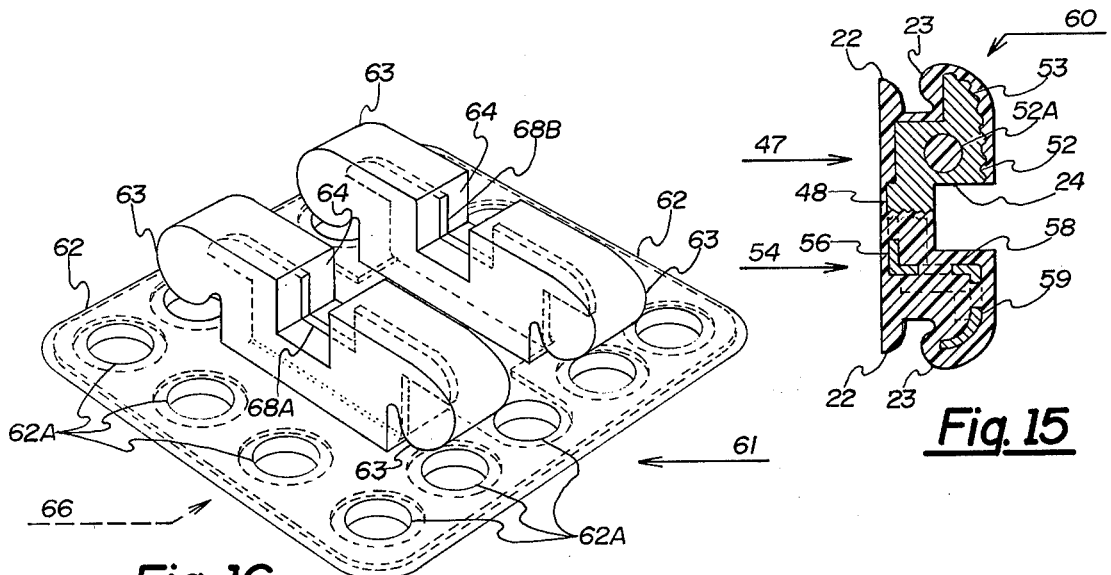
FIG. 15 is a sectional view of an orthodontic bracket with comparative positioning of cores from FIGS. 13 and 14.
FIG. 16 is a perspective view of a bracket of the present invention having an expanded base portion.

Referring to FIG. 15, a comparative cross section of a bracket such as 21 (FIGS. 4, 5 and 6), is shown generally at 60 with juxtaposed halves of core embodiments 47 and 54 (FIGS. 13 and 14, respectively). Bracket 60 has a base 22 with tie wings 23 and an arch wire slot 24. Stiffening core section 47 has a base 48 with a reinforcing riser 52 having an aperture 52 A therein. Reinforcement riser 52 has a tie wing reinforcement extension 53. Stiffening core section 54 has a base 56 with a stiffening riser 58 terminating in a tie wing stiffener extension 59.

Figure 17:
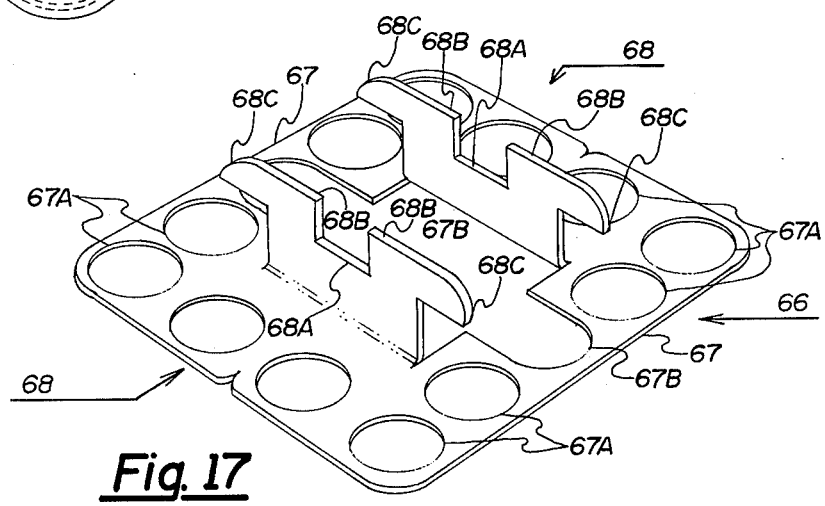
FIG. 17 is a perspective view of the reinforcement core of FIG. 16.

Referring to FIGS. 16 and 17, a bracket assembly for the application of torque is shown at 61 having a base 62 with a plurality of apertures 62A therein. Paired tie wings 63 are shown divided by an arch wire slot 64. A reinforcement core shown generally at 66 has a base 67 containing a plurality of base apertures 67A which are concentric with and, of a larger diameter than, base apertures 62A of bracket 61. Base 67 has a large central aperture with a pair of core riser complexes 68 extending upwardly therefrom. Core riser complexes 68 consist of central slot stiffeners 68A which terminate in slot reinforcing risers 68B having tie wing reinforcements 68C extending therefrom.

OPERATION

Referring back to FIGS. 1, 2 and 3, it can be seen that the prior art non-metallic brackets have no reinforcement members therein and in practice have a tendency to distort excessively according to the forces applied by an arch wire, which in turn tends to decrease or mitigate the overall effect of an arch wire and bracket system. The metallic core illustrated in FIGS. 4, 5 and 6, shows the basic embodiment of the present invention in that the slot area is reinforced which, of course, is the most critical point of force application.

The embodiment shown in FIG. 7 increases the bonding between the metallic stiffening core and the plastic through the use of serrated edges. The embodiments of FIGS. 8 and 9 have included apertures for a plastic flow-through, again increasing the bonding between the plastic and the stiffening cores. The embodiments shown in FIGS. 11 and 12 illustrate techniques for utilizing the instant invention with the straightwire appliance disclosed in U.S. Pat. Nos. 3,660,900 and 3,477,128 issued to Lawrence F. Andrews.

FIGS. 13, 14, 15, 16 and 17 illustrate a tie wing reinforcement section extending from the reinforcement risers to lend more strength to the tie wing area of the bracket. Here again, apertures are utilized to increase the bonding between the core and the plastic of the bracket together with various stamping techniques for creating the reinforcement risers themselves.

It should be understood, of course, that the foregoing disclosure relates to only preferred embodiments of the invention and that it is intended to cover all changes and modifications of the example of the invention herein chosen for the purposes of the disclosure which do not constitute departures from the spirit and scope of the invention.

The invention claimed is:

1. An orthodontic bracket comprising a non-metallic bracket having a front face and a back side and tie wings;

said back side being adapted to be directly secured to the front face of a tooth by means of an adhesive; and said front side having a groove recessed therein for the reception of an arch wire;

and the improvement which comprises:

a stiffening core embedded in the material of said bracket, said stiffening core being constructed of a more rigid metallic material than said non-metallic bracket and being embedded in said non-metallic bracket so that at least one edge of said core is exposed and is not covered by non-metallic bracket material and defines at least one portion of the surface of said arch wire groove.

* * * * *